United States Patent [19]

Lee

[11] 4,346,236

[45] Aug. 24, 1982

[54] METHOD OF OXIDIZING TERTIARY-ALKYL PHOSPHINES

[75] Inventor: Fui-Tseng H. Lee, Princeton, N.J.

[73] Assignee: FMC Corporation, Philadelphia, Pa.

[21] Appl. No.: 232,770

[22] Filed: Feb. 9, 1981

[51] Int. Cl.$^3$ ............................................... C07F 9/53
[52] U.S. Cl. ........................................ 568/15; 568/14
[58] Field of Search .................................... 568/14, 15

[56] References Cited

U.S. PATENT DOCUMENTS

| | | | |
|---|---|---|---|
| 3,082,256 | 3/1963 | Harwood et al. | 260/606.5 |
| 3,145,227 | 8/1964 | Grayson et al. | 260/465.8 |
| 3,325,546 | 6/1967 | Hays | 260/606.5 |
| 3,331,878 | 7/1967 | Priestley | 260/606.5 |
| 3,520,939 | 7/1970 | Brennan | 260/606.5 |
| 3,636,160 | 1/1972 | Carlson | 260/606.5 |
| 3,732,316 | 5/1973 | Lin | 568/14 |
| 3,833,661 | 9/1974 | Ellzey, Jr. et al. | 260/606.5 |
| 3,833,662 | 9/1974 | Staendeke et al. | 568/14 |
| 3,852,362 | 12/1974 | Lambert | 260/606.5 |
| 4,076,755 | 2/1978 | Lippsmeier et al. | 260/606.5 |

OTHER PUBLICATIONS

J.A.C.S. 74, 3282, (1952).
J.A.C.S. 52, 2995, (1930).
Kosolapoff et al., Organic Phosphorus Compounds, Wiley–Intersc., N.Y., pp. 343–349, (1972).

*Primary Examiner*—Helen M. S. Sneed
*Attorney, Agent, or Firm*—Robert W. Kell; Frank Ianno

[57] ABSTRACT

Tertiary-alkyl phosphines, such as tris-(3-hydroxypropyl) phosphine may be oxidized by heating in the presence of water and between about 0.1 and about 10% by weight of an acid catalyst at a temperature above about 100° C.

10 Claims, No Drawings

METHOD OF OXIDIZING TERTIARY-ALKYL PHOSPHINES

The present invention relates to a method of oxidizing tertiary-alkyl phosphines to the corresponding tertiary-alkyl phosphine oxides.

Tris-alkyl phosphine oxides are currently used as flame retardant agents for plastics, are lubricant additives and as flame retardants for hydraulic fluids. As newly discovered applications increase their industrial demand, a reduction in the cost of manufacturing tertiaryl-alkyl phosphine oxides assumes increasing importance.

It is known that phosphines may be oxidized to their corresponding phosphine oxides by air (with or without an initiator) by aqueous alkaline solutions and most effectively by hydrogen peroxide. For example, tris-(hydroxymethyl) phosphine is reported to be completely oxidized to the phosphine oxide when it is treated with air at 50° C. for five hours. Dutch Pat. No. 1040549, issued to Farbwerke Hoechst Aktiengesellschaft Mar. 19, 1959. However, in most cases, air oxidation tends to give products which are complex mixtures of phosphine oxides, phosphites and phosphinates, M. B. Floyd and C. E. Boozer, *J. Am. Chem. Soc.*, 85, 984 (1963).

An oxidation process involving treatment of water soluble tertiary-alkyl phosphines in aqueous solution in air was reported by Lambert and coworkers, Chemical Communications, 870 (1970), U.S. Pat. No. 3,852,362. This process employs a large excess of two normal sodium hydroxide solution (molar ratio of base to phosphine is 20 to 1) and thus requires the later separation of the product from water and base. In addition, the yields of phosphine oxides from this process are low (in the range of 38–75%).

Hydrogen peroxide is known to be the most effective oxidant for the oxidation of phosphines. The peroxide oxidation process has the advantage of giving high yields of clean products and shortening the reaction time. However, the peroxide oxidations are highly exothermic and more expensive than the process to be described.

In accordance with the present invention, a simple process is provided for the oxidation of a water soluble tris-alkyl phosphine to the corresponding tris-alkyl phosphine oxide by heating said phosphine in the presence of water and a catalytic amount of an acid catalyst at a temperature above about 100° C. The amount of catalyst may range from about 0.1% to about 10% of the weight of the phosphine that is oxidized, the preferred catalyst level being about 3% or less. The water soluble phosphines that are oxidized in accordance with the present invention may have the formula:

wherein $A_1$, $A_2$, and $A_3$ are the same or different radicals selected from the group consisting of hydrogen, hydroxyl, hydroxyalkyl, haloalkyl and alkyl radicals, R is an alkyl radical of 1 to 8 carbon atoms, m is 0 or a small whole number (e.g., 1–8) and n is 0, 1 or 2.

The oxidation of tris-3-hydroxypropyl phosphine to tris-(3-hydroxypropyl) phosphine oxide in accordance with the present invention is illustrated by the following reaction:

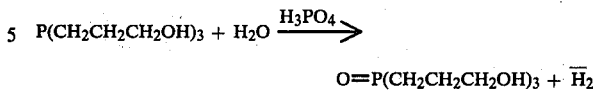

The amount of water that is present in the reaction mixture during the oxidation step may vary from as little as 1 equivalent to a large excess, i.e., 5 or more equivalents. Lesser amounts, e.g., 1 equivalent of water are preferred, however, as it becomes unnecessary to separate the desired phosphine oxide from the water remaining in the reaction mixture.

Both organic and inorganic acids will function as a catalyst in the oxidation reaction. Suitable acids are hydrochloric acid, acetic acid, nitric acid, phosphoric acid, sulfuric acid, methane sulfonic acid, and nitric acid. The stronger acids are preferred as they result in higher yields than are obtained with a weak acid catalyst. Glacial acetic acid is a suitable catalyst but leaves an odor that may be objectional.

At the lower oxidative temperatures, 100° C.–130° C., sulfuric acid is the most active catalyst. However, at higher oxidation temperatures, 150° C.–180° C., differences in the catalytic efficiency diminish and sulfuric acid is only slightly more effective than other acids.

Particularly preferred is phosphoric acid as it results in phosphine oxides that have low odor, good color and low acidity, which may be readily removed. Moreover, any residual phosphoric acid that may be left in the phosphine oxide product will have a minimal effect on the product to which the phosphine oxide is added.

The effective oxidation temperature ranges from about 100° C. to about 200° C. and above, the time required to complete the oxidation being inadversely proportional to the temperature of reaction. The preferred temperature range is from about 150° C. to about 180° C., and at these higher temperatures it is preferred that the reaction be conducted in an autoclave.

As compared with earlier methods for the manufacture of tris-alkyl phosphine oxide, the present invention offers a series of advantages.

The present process is not exothermic and therefore, may be easily controlled without regard to the volume of reactants. No provision need be made to dissipate the heat of reaction by cooling. Moreover, the process described is less costly than is the use of hydrogen peroxide and may be carried out in the absence of solvents. This enables the distillation necessary to eliminate the solvent to be shortened or even dispensed with.

The present invention will be further illustrated by the following examples in which reacting quantities are expressed in parts by weight unless otherwise indicated.

EXAMPLE I

A mixture of tris-(3-hydroxypropyl) phosphine (10.4 g, 0.05 mole) and concentrated hydrochloric acid (0.8 ml of 36% aqueous solution) was purged with nitrogen. The reaction mixture was heated under a nitrogen atmosphere to 120° C. for 4 hours. Heating was continued at this temperature for a total of 27 hours. The gradual disappearance of tris-(3-hydroxypropyl) phosphine was indicated qualitatively by testing with carbon disulfide. A reddish color indicates the presence of a phosphine compound. At 21 hours, only a faint pink color was observed while no color was observed at 27 hours. The reaction mixture was worked up to give a colorless solid product (2.1 g) melted 103° C.–106° C. and identified by spectroscopic analyses to be tris-(3-hydroxypropyl) phosphine oxide (lit. mp=108° C.). A general comparison of different acid catalyst under various conditions may be made from Table I.

EXAMPLE II

A mixture of tris-(3-hydroxypropyl) phosphine (10.4 g, 0.05 mole), concentrated sulfuric acid (1 g) and 1 ml of water was purged with nitrogen. The reaction mixture was heated under a nitrogen atmosphere at 110° C. for 6 hours. At the end of that time, the amount of residual phosphine tris-(3-hydroxypropyl) phosphine was determined by the addition of an excess of hydrogen peroxide (3% hydrogen peroxide) and titration of the residual unreacted hydrogen peroxide with 0.1 N ceric sulfate solution. Fifty-two percent of the starting tris-(3-hydroxypropyl) phosphine was oxidized to the corresponding phosphine oxide. A general comparison of sulfuric acid with other acid catalyst under various conditions may be made from Table I.

EXAMPLE III

The process described in Example II above is repeated by reacting at 110° C. (10.4 g, 0.05 mole) tris-(3-hydroxypropyl) phosphine, concentrated nitric acid (0.8 ml of 70% aqueous solution) and 1 ml of water. The yield after 32 hours (determined by the addition of an excess of 3% hydrogen peroxide solution and back titration with 0.1 N ceric sulfate) was 64%. A general comparison of the effect of nitric acid catalyst with other catalyst under various conditions may be made from Table I.

EXAMPLE IV

The process described in Example II above is repeated by reacting at 120° C. (10.4 g, 0.05 mole) tris-(3-hydroxypropyl) phosphine, concentrated phosphoric acid (0.6 ml of 86% aqueous solution) and 1 ml of water. The yield after 5 hours (determined by the addition of an excess of hydrogen peroxide solution and back titration with 0.1 N ceric sulfate) was 75%. A general comparison of the effect of phosphoric acid catalyst with other catalyst under various conditions may be made from Table I.

EXAMPLE V (A) The effect of the amount of concentrated sulfuric acid catalyst at low temperatures was demonstrated by repeating Example II above and reducing the amount of concentrated sulfuric acid to 5 weight percent of the tris-(3-hydroxypropyl) phosphine. The yield after 6 hours at 110° C. (determined by the addition of an excess of 3% hydrogen peroxide solution and back titration with 0.1 N ceric sulfate) was 95.7%.

(B) Example V(A) was repeated with 0.26 g of concentrated sulfuric acid [2.5% of the tris-(3-hydroxypropyl) phosphine]. When the concentration of sulfuric acid is reduced to 2.5% and the reaction temperature is increased to 120° C. the yield after 5½ hours, was found to be 74%.

(C) Example V(B) was repeated with the same amount of concentrated sulfuric acid [0.26 g or 2.5% of the tris-(3-hydroxypropyl) phosphine] but the reaction was run in an autoclave and the temperature was increased to 140° C. The yield after 5 hours (determined by the addition of an excess of 3% hydrogen peroxide solution and back titration with 0.1 N ceric sulfate) was 99%.

The tris-(3-hydroxypropyl) phosphine oxide was a free flowing solid.

EXAMPLE VI

The effect of concentrated phosphoric acid in amounts of 1 to 2.5 weight percent was determined by reacting in an autoclave (10.4 g, 0.05 mole) of tris-(3-hydroxypropyl) phosphine, concentrated phosphoric acid (0.15, 0.14 and 0.06 ml of 86% aqueous solution) and 1 ml of water. The yields of tris(3-hydroxypropyl) phosphine oxide after 4.5 to 5 hours at temperatures between 150° C. and 180° C. is summarized in Table III.

The tris-(3-hydroxypropyl) phosphine oxide prepared at 180° C. [VI(C)] was a colorless and odorless free flowing solid.

EXAMPLE VII s-Butyl bis(3-Hydroxypropyl) Phosphine Oxide

Into a one gallon stainless steel pressure reactor was placed 224 g (4 moles) of mixed 2-butene, 600 ml of toluene, 204 g (6.0 moles, 50% excess) of phosphine and 25 ml of a solution of 4 g azobisisobutyronitrile in 100 ml of toluene. The reaction vessel was heated and stirred at 85° C. to 90° C. for one hour and the remaining azobisisobutyronitrile solution is added in 25 ml portions every 30 minutes until the 100 ml of catalyst solution is used up. The reaction mixture was heated and stirred at 90° C. for 4 hours after the last addition of catalyst solution and then allowed to cool overnight.

The phosphine was vented from the reaction vessel and 487 g (8.4 moles, 5% excess) allyl alcohol was added together with 50 ml of a solution of 8 g azobisisobutyronitrile in 200 ml of toluene. The reaction mixture was heated with stirring at 90° C. with the addition of 50 ml azobisisobutyronitrile catalyst solution every 30 minutes until all 200 ml of solution had been added. Heating and stirring were continued at 90° C. for 4 hours and the reaction vessel was then allowed to cool to room temperature. The liquid from the reaction vessel was heated to 130° C./1.5 mm to remove volatile components. The residual product, s-butyl bis(3-hydroxypropyl) phosphine, was a greenish liquid weighing 519.3 g.

A mixture of s-butyl bis(3-hydroxypropyl) phosphine (103 g, 0.5 mole), 1 g concentrated (86%) phosphoric acid and 10.8 g (0.55 mole) water were heated in an autoclave at 180° C. for 5 hours. The resulting product was analyzed and found to contain 93% by weight s-butyl bis(3-hydroxypropyl) phosphine oxide.

EXAMPLE VIII

Methyl phosphine may be prepared by the method of Wagner et al, *J. Am. Chem. Soc.*, 75, 3869 (1953). The methyl phosphine may then be reacted with an excess of allyl alcohol in a pressure vessel and in the presence of azobisisobutyronitrile to form methyl bis(3-hydroxypropyl) phosphine. The phosphine may then be oxidized to the corresponding phosphine oxide by heating in a pressure vessel at 180° C. with 2.5 weight percent concentrated (86%) phosphoric acid and 1.5 equivalents of water.

TABLE I

| No. | Catalyst (Weight %) | Reaction Temp. °C. | Reaction Time, Hrs. | Unoxidized (Weight %) |
| --- | --- | --- | --- | --- |
| 0 | No Catalyst | 180* | 5 | 40 |
| 1 | Conc. HCl 9% | 120 | 27 | 12 |
| 2 | Conc. H$_2$SO$_4$ 10% | 110 | 6 | 4.8 |
| 3 | Conc. HNO$_3$ 7% | 110 | 32 | 36 |
| 4 | Conc. H$_3$PO$_4$ 9% | 120 | 5 | 25 |

*Reaction was carried out in a pressurized vessle.

TABLE II

| No. | Conc. H$_2$SO$_4$ (Weight %) | Reaction Temp. °C. | Reaction Time, Hrs. | Unoxidized (Weight %) |
| --- | --- | --- | --- | --- |
| 2 | 10 | 110 | 6 | 4.8 |
| 5(A) | 5 | 110 | 7 | 4.3 |
| 5(B) | 2.5 | 120 | 5½ | 26 |
| 5(C) | 2.5 | 140 | 5 | 1 |

TABLE III

| No. | Conc. H$_3$PO$_4$ (Weight %) | Reaction Temp. °C. | Reaction Time, Hrs. | Unoxidized (Weight %) |
| --- | --- | --- | --- | --- |
| VI A | 2.5 | 150 | 4.5 | 11 |
| VI B | 2.4 | 160 | 5 | 1.6 |
| VI C | 1.0 | 180 | 5 | 2.7 |

I claim:

1. A process for the oxidation of a water soluble tris-alkyl phosphine to the corresponding tris-alkyl phosphine oxide which comprises heating said phosphine in the presence of water and catalytic amounts of an acid at a temperature above about 100° C.

2. The process of claim 1 wherein said tris-alkyl phosphine has the formula:

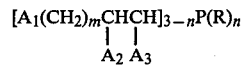

wherein A$_1$, A$_2$, and A$_3$ are the same or different radicals selected from the group consisting of hydrogen, hydroxyl, hydroxyalkyl, haloalkyl and alkyl radicals, R is an alkyl radical of 1 to 8 carbon atoms, m is 0 or a small whole number and n is 0, 1 or 2.

3. The process of claim 1 wherein said alkyl phosphine is sec-butyl bis-(3-hydroxypropyl) phosphine.

4. The process of claim 1 wherein said tris-alkyl phosphine is tris(3-hydroxy-2-methylpropyl) phosphine.

5. The process of claim 1 wherein said tris-alkyl phosphine is tris(3-hydroxypropyl) phosphine.

6. The process of claim 1 wherein said catalyst is hydrochloric acid.

7. The process of claim 1 wherein said catalyst is sulfuric acid.

8. The process of claim 1 wherein said catalyst is phosphoric acid.

9. The process of claim 1 wherein said acid is methane sulfonic acid.

10. The process of claim 1 wherein said acid is glacial acetic acid.

* * * * *